(12) United States Patent
Crane et al.

(10) Patent No.: US 10,898,416 B2
(45) Date of Patent: Jan. 26, 2021

(54) COMPOSITIONS CONTAINING AN OPTIMIZED EMULSIFIER SYSTEM

(71) Applicant: L'ORÉAL, Paris (FR)

(72) Inventors: Christine Marie Crane, Watchung, NJ (US); Angeles Clara Fonolla-Moreno, Rio de Janeiro (BR); Omotayo Awofesobi, West Orange, NJ (US); Alice Monique Rosine Lefebvre, Rahway, NJ (US)

(73) Assignee: L'OREAL, Paris (FR)

( * ) Notice: Subject to any disclaimer, the term of this patent is extended or adjusted under 35 U.S.C. 154(b) by 292 days.

(21) Appl. No.: 15/418,017

(22) Filed: Jan. 27, 2017

(65) Prior Publication Data

US 2018/0214355 A1 Aug. 2, 2018

(51) Int. Cl.
| | | |
|---|---|---|
| *A61K 8/06* | (2006.01) |
| *A61Q 1/10* | (2006.01) |
| *A61K 8/81* | (2006.01) |
| *A61K 8/92* | (2006.01) |
| *A61K 8/37* | (2006.01) |
| *A61K 8/34* | (2006.01) |
| *A61K 8/46* | (2006.01) |
| *A61K 8/69* | (2006.01) |

(52) U.S. Cl.
CPC .............. *A61K 8/062* (2013.01); *A61K 8/342* (2013.01); *A61K 8/375* (2013.01); *A61K 8/463* (2013.01); *A61K 8/69* (2013.01); *A61K 8/8123* (2013.01); *A61K 8/922* (2013.01); *A61Q 1/10* (2013.01); *A61K 2800/30* (2013.01)

(58) Field of Classification Search
CPC .......... A61K 8/062; A61K 8/31; A61K 8/342; A61K 8/731; A61K 8/8152; A61K 8/86; A61K 8/891; A61K 8/892; A61K 8/895; A61Q 1/10

See application file for complete search history.

(56) References Cited

U.S. PATENT DOCUMENTS

| 3,251,740 A | 5/1966 | Kambersky | |
| 2004/0009201 A1 * | 1/2004 | Collin | ..................... A61K 8/044 424/401 |
| 2005/0042191 A1 | 2/2005 | Travkina et al. | |
| 2015/0079015 A1 * | 3/2015 | Bolognini | ............ A61K 8/8152 424/70.7 |
| 2015/0079016 A1 | 3/2015 | Bolognini et al. | |

OTHER PUBLICATIONS

Masters et al. (Reinforcing sound management throughtrade: shea tree products in Africa; Unasylva 219, vol. 55, 2004).*

* cited by examiner

*Primary Examiner* — Anna R Falkowitz
(74) *Attorney, Agent, or Firm* — Oblon, McClelland, Maier & Neustadt, L.L.P.

(57) ABSTRACT

The invention relates to a composition, especially a cosmetic composition, including water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16), with the compositions further including at least one colorant and/or excluding wax, as well as to methods of using such compositions.

20 Claims, No Drawings

COMPOSITIONS CONTAINING AN OPTIMIZED EMULSIFIER SYSTEM

FIELD OF THE INVENTION

The present invention relates to compositions comprising water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16). Preferably, the compositions further comprise at least one colorant and/or are free of wax.

DISCUSSION OF THE BACKGROUND

Many cosmetic compositions, including pigmented cosmetics such as foundations, concealers, lipsticks, and mascaras, and other cosmetic and sunscreen compositions, have been formulated in an attempt to impart desired cosmetic properties. For example, mascaras typically contain wax which is used to provide body and volume. However, the tackiness of the wax leads to mascara compositions that clump, apply unevenly, quickly dry the lashes, smudge, flake and are difficult to remove. Also, the tackiness of the wax limits the playtime (smoothness) of these waxes. When wax is eliminated from the mascaras, application and removal are facilitated, but the compositions lose desirable properties and tend to be runny.

Further, typically the addition of oils to traditional wax-containing mascara formulations (anhydrous or water-containing) can impact negatively the wear of the formula on the lashes, such that the mascara will smudge more.

U.S. Pat. No. 3,251,740 and U.S. patent application publication nos. 2005/0042191, 2015/0079015 and US2015/0079016 disclose mascara products of different composition.

However, there remains a need for improved cosmetic compositions having improved cosmetic properties, particularly mascaras and particularly water-containing mascaras, which are long-wearing, volumizing, possess low flake properties and/or possess low smudging properties.

Accordingly, one aspect of the present invention is a water-containing care and/or makeup and/or treatment composition for keratinous material which has good cosmetic properties such as, for example, good long-wearing properties, good volumizing properties, low flaking properties and/or low smudging properties.

SUMMARY OF THE INVENTION

The present invention relates to compositions for keratinous material (for example, eyebrows and/or eyelashes) comprising water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16). Preferably, the composition further comprises at least one coloring agent and/or is a mascara composition. Also preferably, the composition is free of wax.

The present invention also relates to methods of treating, caring for and/or making up keratinous material (for example, eyebrows and/or eyelashes) by applying compositions of the present invention comprising water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16), to the keratinous material in an amount sufficient to treat, care for and/or make up the keratinous material. Preferably, the composition further comprises at least one coloring agent and/or is a mascara composition. Also preferably, the composition is free of wax.

The present invention also relates to methods of enhancing the appearance of keratinous material (for example, eyebrows and/or eyelashes) by applying compositions of the present invention comprising water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16), to the keratinous material in an amount sufficient to enhance the appearance of the keratinous material. Preferably, the composition further comprises at least one coloring agent and/or is a mascara composition. Also preferably, the composition is free of wax.

The present invention further relates to kits containing a composition of the present invention comprising water, at least one film-forming agent, at least one volumizing agent, and an emulsification system comprising (i) about 2% to about 6% of low HLB emulsifier(s) (HLB value less than 8), (ii) about 2% to about 8% of intermediate HLB emulsifier(s) (HLB value of 8 to 16), and (iii) about 1% to about 8% of high HLB emulsifier(s) (HLB value greater than 16). Preferably, the composition further comprises at least one coloring agent and/or is a mascara composition. Also preferably, the composition is free of wax. Preferably, the kit comprises (i) a mascara composition and (ii) a topcoat composition and/or a basecoat composition.

It is to be understood that both the foregoing general description and the following detailed description are exemplary and explanatory only, and are not restrictive of the invention.

DETAILED DESCRIPTION OF THE INVENTION

In the following description of the invention and the claims appended hereto, it is to be understood that the terms used have their ordinary and accustomed meanings in the art, unless otherwise specified.

"About" as used herein means within 10% of the indicated number (e.g. "about 10%" means 9%-11% and "about 2%" means 1.8%-2.2%).

"A" or "an" as used herein means "at least one."

As used herein, all ranges provided are meant to include every specific range within, and combination of subranges between, the given ranges. Thus, a range from 1-5, includes specifically 1, 2, 3, 4 and 5, as well as subranges such as and 2-5, 3-5, 2-3, 2-4, 1-4, etc.

"Film former", "film-forming polymer" or "film-forming agent" or "co-film former" as used herein means a polymer or resin that leaves a film on the substrate to which it is applied, for example, after a solvent accompanying the film former has evaporated, absorbed into and/or dissipated on the substrate.

"Wax" as used herein is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state.

"Free" or "devoid" of as it is used herein means that while it is preferred that no amount of the specific component be present in the composition, it is possible to have very small amounts of it in the compositions of the invention provided that these amounts do not materially affect at least one, preferably most, of the advantageous properties of the compositions of the invention. Thus, for example, "free of solvents" means that non-aqueous solvents are preferably omitted (that is 0% by weight), but can be present in the composition at an amount of less than about 0.1% by weight, typically less than about 0.05% by weight, based on the total weight of the composition.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to keratin materials such as eyelashes and evaluating the color of the composition after an extended period of time. For example, the color of a composition may be evaluated immediately following application to keratin materials such as eyelashes and these characteristics may then be re-evaluated and compared after a certain amount of time. Further, these characteristics may be evaluated with respect to other compositions, such as commercially available compositions.

"Making up" as used herein means to provide decoration (for example, color) to keratin materials such as the eyelashes.

"Protecting" as used herein means to inhibit damage to keratin materials such as the eyelashes by providing a protective layer on the keratin materials.

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalkyl groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Water-resistance" as used herein, means resistance of a material (substance) to the penetration of water, which may cause degradation of that material. The method implemented if assessment of this invention is further disclosed.

"Transfer-resistance" as used herein refers to the quality exhibited by compositions that are not readily removed by contact with another material, such as, for example, a glass, an item of clothing or the skin, for example, when eating or drinking. Transfer resistance may be evaluated by any method known in the art for evaluating such. For example, transfer resistance of a composition may be evaluated by a "kiss" test. The "kiss" test may involve application of the composition to human keratin material such as hair, skin or lips followed by rubbing a material, for example, a sheet of paper, against the hair, skin or lips after expiration of a certain amount of time following application, such as 2 minutes after application. Similarly, transfer resistance of a composition may be evaluated by the amount of product transferred from a wearer to any other substrate, such as transfer from the hair, skin or lips of an individual to a collar when putting on clothing after the expiration of a certain amount of time following application of the composition to the hair, skin or lips. The amount of composition transferred to the substrate (e.g., collar, or paper) may then be evaluated and compared. For example, a composition may be transfer resistant if a majority of the product is left on the wearer's hair, skin or lips. Further, the amount transferred may be compared with that transferred by other compositions, such as commercially available compositions. In a preferred embodiment of the present invention, little or no composition is transferred to the substrate from the hair, skin or lips.

The compositions and methods of the present invention can comprise, consist of, or consist essentially of the essential elements and limitations of the invention described herein, as well as any additional or optional ingredients, components, or limitations described herein or otherwise useful.

Referred to herein are trade names for materials including, but not limited to polymers and optional components. The inventors herein do not intend to be limited by materials described and referenced by a certain trade name. Equivalent materials (e.g., those obtained from a different source under a different name or catalog (reference) number) to those referenced by trade name may be substituted and utilized in the methods described and claimed herein.

All percentages and ratios are calculated by weight unless otherwise indicated. All percentages are calculated based on the total weight of a composition unless otherwise indicated. All component or composition levels are in reference to the active level of that component or composition, and are exclusive of impurities, for example, residual solvents or by-products, which may be present in commercially available sources.

Water

According to present invention, compositions comprising water are provided. Preferably, compositions of the present invention comprise from about 5% to about 90% water, preferably from about 15% to about 80% water, preferably from about 20% to about 70% water, and preferably from about 30% to about 60% water by weight with respect to the total weight of the composition, including all ranges and subranges therebetween. Preferably, the compositions of the present invention are in the form of an emulsion, with a simple emulsion such as an oil-in-water (O/W) being the most preferred form.

Film-Forming Agent

According to the present invention, compositions comprising at least one film-forming agent are provided. According to preferred embodiments, the compositions of the present invention comprise at least one dispersion of film forming particles in aqueous phase. The dispersion of film forming particles in aqueous phase is more generally known as latex.

Suitable polymers for the film-forming particles that may be used in the compositions of the present invention include, but are not limited to, synthetic polymers, free-radical type or polycondensate type polymers, polymers of natural origin, and mixtures thereof.

Preferably, the polymers for the film-forming particles may be selected from vinyl (co)polymers, (meth)acrylic (co)polymers, urethanes (co)polymers, and mixtures thereof. Advantageously, the polymer for the film-forming particles is selected from a styrene-(meth)acrylic and (meth) acrylic copolymer, a vinyl acetate and (meth)acrylic copolymer, and mixtures thereof.

Polymers for the film-forming particles of the free-radical type may be chosen, for example, from vinyl polymers or copolymers, such as acrylic polymers.

Vinyl film-forming polymers can result from the polymerization of monomers comprising at least one ethylenic unsaturation and at least one acidic group and/or esters of these acidic monomers and/or amides of these acidic monomers. Monomers comprising at least one acid group which may be used include, for example, $\alpha,\beta$-ethylenic unsaturated carboxylic acids such as acrylic acid, methacrylic acid, crotonic acid, maleic acid or itaconic acid. (Meth)acrylic acid and crotonic acid are, for example, used. Preferably, (meth)acrylic acid is used.

The esters of acidic monomers can be chosen, for example, from (meth)acrylic acid esters (also known as (meth)acrylates), such as (meth)acrylates of an alkyl, for example, a C1-C30 alkyl, such as a C1-C20 alkyl, (meth) acrylates of an aryl, such as a C6-010 aryl, and (meth) acrylates of a hydroxyalkyl, such as a C2-C6 hydroxyalkyl. Among the alkyl (meth)acrylates that may be mentioned, examples include methyl methacrylate, ethyl methacrylate, butyl methacrylate, isobutyl methacrylate, 2-ethylhexyl methacrylate, lauryl methacrylate and cyclohexyl methacrylate. Among the hydroxyalkyl (meth)acrylates that may be mentioned, examples include hydroxyethyl acrylate, 2-hydroxypropyl acrylate, hydroxyethyl methacrylate and 2-hydroxypropyl methacrylate. Among the aryl (meth)acrylates that may be mentioned, examples include benzyl acrylate and phenyl acrylate. The (meth)acrylic acid esters that may be used are, for example, alkyl (meth)acrylates.

The alkyl group of the esters may be substituted. For example, the alkyl group of the esters may be either fluorinated or perfluorinated, i.e., some or all of the hydrogen atoms of the alkyl group are substituted with fluorine atoms. Further, examples of amides of the acid monomers that may be mentioned include (meth)acrylamides, such as N-alkyl (meth)acrylamides, for example, of a $C_2$-$C_{12}$ alkyl. Among the N-alkyl(meth)acrylamides that may be mentioned, examples include N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. For example, these monomers may be polymerized with acid monomers and/or esters thereof and/or amides thereof, such as those mentioned above. Examples of vinyl esters that may be mentioned include vinyl acetate, vinyl neodecanoate, vinyl pivalate, vinyl benzoate and vinyl t-butylbenzoate. Styrene monomers that may be mentioned include styrene and $\alpha$-methylstyrene.

Among the film-forming polycondensates that may be mentioned, examples include polyurethanes, polyesters, polyesteramides, polyamides, epoxyester resins and polyureas, and modifications or derivatives of any of these.

The polyurethanes may be chosen from anionic, cationic, nonionic or amphoteric polyurethanes, polyurethane-acrylics, polyurethane-polyvinylpyrrolidones, polyester-polyurethanes, polyether-polyurethanes, polyureas and polyurea-polyurethanes, and mixtures thereof.

The polyesters may be obtained, in a known manner, by polycondensation of dicarboxylic acids with polyols, such as diols.

The dicarboxylic acid may be aliphatic, alicyclic or aromatic. Examples of such acids that may be mentioned include: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalene-dicarboxylic acid and 2,6-naphthalenedicarboxylic acid. These dicarboxylic acid monomers may be used alone or as a combination of at least two dicarboxylic acid monomers. Among these monomers, phthalic acid, isophthalic acid and terephthalic acid may, for example, be used.

The diol may be chosen from aliphatic, alicyclic and aromatic diols. The diol used is, for example, chosen from ethylene glycol, diethylene glycol, triethylene glycol, 1,3-propanediol, cyclohexanedimethanol and 4-butanediol. Other polyols that may be used include glycerol, pentaerythritol, sorbitol and trimethylolpropane.

The polyesteramides may be obtained in a manner analogous to that of the polyesters, by polycondensation of diacids with diamines or amino alcohols. Diamines that may be used include, for example, ethylenediamine, hexamethylenediamine and meta- or para-phenylenediamine. An amino alcohol that may be used is, for example, monoethanolamine.

The polyester may also comprise at least one monomer bearing at least one —$SO_3M$ group, wherein M is chosen from a hydrogen atom, an ammonium ion $NH_4^+$ and a metal ion such as an $Na^+$, $Li^+$, $K^+$, $Mg^{2+}$, $Ca^{2+}$, $Cu^{2+}$, $Fe^{2+}$ or $Fe^{3+}$ ion. A difunctional aromatic monomer comprising such an —$SO_3M$ group may, for example, be used.

The aromatic nucleus of the difunctional aromatic monomer also comprising an —$SO_3M$ group as described above may be chosen, for example, from benzene, naphthalene, anthracene, biphenyl, oxybiphenyl, sulfonylbiphenyl and methylenebiphenyl nuclei. Among the difunctional aromatic monomers also comprising an $SO_3M$ group, mention may be made, for example, of sulfoisophthalic acid, sulfoterephthalic acid, sulfophthalic acid, 4-sulfonaphthalene-2,7-dicarboxylic acid.

The copolymers used are, for example, those based on isophthalate/sulfoisophthalate, such as copolymers obtained by condensation of diethylene glycol, cyclohexanedimethanol, isophthalic acid and sulfoisophthalic acid.

The polymer for the film forming particles may also be a liposoluble polymer. Examples of the liposoluble polymer that may be mentioned include copolymers of a vinyl ester (wherein the vinyl group is directly linked to the oxygen atom of the ester group and the vinyl ester comprises a radical chosen from saturated, linear or branched hydrocarbon-based radicals of 1 to 19 carbon atoms, linked to the carbonyl of the ester group) and of at least one other monomer, which may be a vinyl ester (different from the vinyl ester already present), an $\alpha$-olefin (comprising from 8 to 28 carbon atoms), an alkyl vinyl ether (the alkyl group of which comprises from 2 to 18 carbon atoms) or an allylic or methallylic ester (comprising a radical chosen from saturated, linear or branched hydrocarbon-based radicals of 1 to 19 carbon atoms, linked to the carbonyl of the ester group).

These copolymers may be crosslinked using crosslinking agents that may be either of the vinylic type or of the allylic or methallylic type, such as tetraallyloxyethane, divinylbenzene, divinyl octanedioate, divinyl dodecanedioate and divinyl octadecanedioate.

Examples of these copolymers which may be mentioned include the following copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, crosslinked with 0.2% divinylbenzene, vinyl dimethylpropionate/vinyl laurate, crosslinked with 0.2% divinylbenzene, vinyl acetate/octadecyl vinyl ether, crosslinked with 0.2% tetraallyloxyethane, vinyl acetate/allyl stearate, crosslinked with 0.2% divinylbenzene, vinyl acetate/1-octadecene, crosslinked with 0.2% divinylbenzene, and allyl propionate/allyl stearate, crosslinked with 0.2% divinylbenzene.

Further examples of the liposoluble film-forming polymers include liposoluble copolymers, such as those resulting from the copolymerization of vinyl esters comprising from 9 to 22 carbon atoms or of alkyl acrylates or methacrylates, wherein the alkyl radicals comprise from 10 to 20 carbon atoms. Such liposoluble copolymers may be chosen, for example, from polyvinyl stearate, polyvinyl stearate crosslinked with the aid of divinylbenzene, of diallyl ether or of diallyl phthalate copolymers, polystearyl (meth)acrylate, polyvinyl laurate and polylauryl (meth)acrylate copolymers, it being possible for these poly(meth)acrylates to be crosslinked with the aid of ethylene glycol dimethacrylate or tetraethylene glycol dimethacrylate. The liposoluble copolymers described above are known and are described, for example, in French patent application FR-A-2 232 303; they may have a weight-average molecular weight ranging, for example, from 2,000 to 500,000 such as from 4,000 to 200,000.

Among the liposoluble film-forming polymers which may be used herein, mention may also be made, for example, of polyalkylenes such as copolymers of $C_2$-$C_{20}$ alkenes, such as polybutene, alkylcelluloses with a linear or branched, saturated or unsaturated $C_1$-$C_8$ alkyl radical, for instance ethylcellulose and propylcellulose, copolymers of vinylpyrrolidone (VP) such as copolymers of vinylpyrrolidone and of $C_2$-$C_{40}$ alkene such as $C_3$-$C_{20}$ alkene. Among the VP copolymers which may be used herein, mention may be made, for example, of the copolymers of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate.

Specific examples of aqueous dispersions of film-forming particles which may be used are the acrylic dispersions sold under the names "Neocryl XK-90®", "Neocryl A-1070®", "Neocryl A-10900", "Neocryl BT-62®", "Neocryl A-10790" and "Neocryl A-5230" by the company Avecia-Neoresins, "Dow Latex 4320" by the company Dow Chemical, "Daitosol 5000 ADO" or "Daitosol 5000 SJ" by the company Daito Kasey Kogyo; the aqueous dispersions of polyurethane sold under the names "Neorez R-981®" and "Neorez R-974®" by the company Avecia-Neoresins, "Avalure UR-405®", "Avalure UR-410®", "Avalure UR-4250", "Avalure UR-4500", "Sancure 8750", "Sancure 8610", "Sancure 878®" and "Sancure 2060®" by the company Goodrich, "Impranil 850" by the company Bayer and "Aquamere H-151®" by the company Hydromer; vinyl dispersions, for instance "Mexomer PAM" and also acrylic dispersions in isododecane, for instance "Mexomer PAP" by the company Chimex.

Further specific examples of latex polymers for use in the present invention further include ethylhexyl acrylate/hema copolymer (and) acrylatesidiethylaminoethyl methacrylate/ethylhexyl acrylate copolymer (Syntran®PC 5775), styrene/acrylates/ammonium methacrylate copolymer (Syntran®5760, Syntran®5009, Syntran®PC5620), polyacrylate-21 (and) acrylates/dimethylaminoethyl methacrylate copolymer (Syntran®PC5100, Syntran®PC5776, Eudragit®E 100, Jurymer ET-410C), styrene/acrylates/ammonium methacrylate copolymer (Syntran®5009 CG), olefin/acrylate grafted polymer (and) sodium laureth sulfate (and C12-15 SEC-pareth 15 (Syntran®EX108), acrylates copolymer (Aculyn®33A Polymer, Avalure®Ace 210/120/315 Acrylic Copolymer, Carbopol® Aqua SF-1 Polymer, Coatex®Co 633, Eliclear®380/700/4U, Eudragit® L 100, Joncryl®85, Luviflex®Soft), acrylates/ethylhexyl acrylate copolymer. The Syntran® polymers are commercially available from the supplier Interpolymer Corp.

According to preferred embodiments, compositions of the present invention may comprise instead of, or in addition to, the dispersion of film forming particles in aqueous phase discussed above one or more film-forming agents suitable for use in compositions for application to eyebrows and/or eyelashes. Such film-forming agents can be, for example, water-soluble or liposoluble. Acceptable film-forming are known in the art and include, but are not limited to, those disclosed in U.S. patent application publication no. 2004/0170586, the entire contents of which is hereby incorporated by reference.

Specific examples of film-forming agents include, but are not limited to, proteins, such as proteins of plant origin, such as, for example, wheat or soya proteins; or proteins of animal origin, such as keratins, for example keratin hydrolysates and sulfonic keratins; cellulose polymers, such as, for example, hydroxyethylcellulose, hydroxypropylcellulose, methylcellulose or ethylhydroxyethylcellulose; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates, and mixtures thereof.

Specific examples of suitable film-forming agents also include silicone resins such as, for example, MQ resins (for example, trimethylsiloxysilicates), T-propyl silsesquioxanes and MK resins (for example, polymethylsilsesquioxanes), silicone esters such as those disclosed in U.S. Pat. Nos. 6,045,782, 5,334,737, and 4,725,658, the disclosures of which are hereby incorporated by reference, polymers comprising a backbone chosen from vinyl polymers, methacrylic polymers, and acrylic polymers and at least one chain chosen from pendant siloxane groups and pendant fluorochemical groups such as those disclosed in U.S. Pat. Nos. 5,209,924, 4,693,935, 4,981,903, 4,981,902, and 4,972,037, and WO 01/32737, the disclosures of which are hereby incorporated by reference, polymers such as those described in U.S. Pat. No. 5,468,477, the disclosure of which is hereby incorporated by reference (a non-limiting example of such polymers is poly(dimethylsiloxane)-g-poly(isobutyl methacrylate), which is commercially available from 3M Company under the tradename VS 70 IBM), and mixtures thereof.

Specific examples of suitable polymers further include, but are not limited to, polyalkylenes, polyvinylpyrrolidone (PVP) or vinylpyrrolidone (VP) homopolymers or copolymers, copolymers of a $C_2$ to $C_{30}$, such as $C_3$ to $C_{22}$ alkene, and combinations thereof. As specific examples of VP copolymers which can be used in the invention, mention may be made of VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene or VP/acrylic acid/lauryl methacrylate copolymer, and mixtures thereof.

Preferably, the film-forming polymers are present in the compositions of the present invention in an amount sufficient to form a film upon a substrate to which it has been applied (for example, eyebrows and/or eyelashes).

So, for example, when film-forming particles are present in the composition and are in the form of a commercial product containing the film-forming particles in aqueous dispersion, the amount of active material (that is, film-forming particles) within the aqueous dispersion is sufficient to form a film upon a substrate to which it has been applied.

Preferably, the film-forming polymer(s) is/are present in the compositions of the present invention in amounts of active material (e.g., solid content) generally ranging from about 1% to about 40%, preferably from about 5% to about 30%, and preferably from about 7% to about 20%, by weight, based on the total weight of the composition, including all ranges and subranges in between.

Volumizing Agent

According to the present invention, compositions comprising at least one volumizing agent selected from the group consisting of inert fillers, glyceryl esters of fatty acids, and mixtures thereof, are provided.

Regarding inert fillers, any suitable inert filler may be used in accordance with the present invention. The term "inert filler" means any particle that is solid at room temperature and atmospheric pressure which does not react chemically with the various ingredients of the composition and which is insoluble in these ingredients.

The at least one inert filler preferably has a melting point which is greater than 150° C., preferably greater than 170° C., preferably greater than 200° C., preferably greater than 250° C., and preferably greater than 300° C.

The at least one inert filler may or may not be absorbent, i.e., capable in particular of absorbing the oils of the composition.

The at least one inert filler may have an apparent diameter ranging from 0.01 µm to 150 µm, preferably from 0.1 µm to 120 µm, preferably from 0.5 µm to 80 µm, preferably from 0.75 µm to 40 µm, and preferably from 1 µm to 10 µm, including all ranges and subranges therebetween. An apparent diameter corresponds to the diameter of the circle into which the elementary particle fits along its shortest dimension (thickness for leaflets).

The at least one inert filler may be mineral or organic, and lamellar, spherical or oblong. The at least one inert filler may be chosen from talc, mica, silica, kaolin, polyamide powders such as Nylon® powder, poly-β-alanine powder, polyethylene powder, acrylic polymer powder and in particular polymethyl methacrylate (PMMA) powder, for instance the product sold or made by Wacker under the reference Covabead LH-85 (particle size 10-12 µm) or acrylic acid copolymer powder (Polytrap® from Dow Corning), polytetrafluoroethylene (Teflon®) powders, lauroyllysine, boron nitride, starch, hollow polymer microspheres such as those of polyvinylidene chloride/acrylonitrile, for instance Expancel® (Nobel Industrie), hollow polymer microspheres (Tospearl® from Toshiba, for example), precipitated calcium carbonate, magnesium carbonate and hydrocarbonate, hydroxyapatite, hollow silica microspheres, glass or ceramic microcapsules and polyester particles.

Regarding glyceryl esters of fatty acid, any suitable triglyceride fatty acid ester may be used in accordance with the present invention. Fatty acids correspond the formula R—COOH, in which R denotes a saturated or unsaturated hydrocarbon radical preferably having from 7 to 45 carbon atoms, preferably from 9 to 35 carbon atoms, preferably from 15 to 35 carbon atoms, preferably from 15 to 21 carbon atoms, and preferably from 16 to 18 carbon atoms. Mention may be made of, for example, palmitic acid, stearic acid, oleic acid, ricinoleic acid, linoleic acid, linolenic acid, arachidic acid, and mixtures thereof.

Triglyceride fatty acid esters result from the reaction of the three alcohol functional groups of glycerol with fatty acids, it being possible for these fatty acids to be identical or different.

Particularly preferred as a source of glyceryl esters of fatty acid in accordance with the present invention is shea butter which contains, among other things, glyceryl esters of stearic acid (in an amount of 20%-50% by weight of shea butter) and oleic acid (in an amount of 40%-60% by weight or shea butter). Shea butter contains higher levels of glyceryl esters of steric acid (preferred, 40-47%) in contrast to common oils that contain mostly glyceryl esters of unsaturated fats.

If present, shea butter is preferably present in an amount ranging from about 1% to about 20%, preferably from about 2% to about 15%, and preferably from about 3.5% to about 10%, by weight, based on the total weight of the composition, including all ranges and subranges in between.

Preferably, when the volumizing agent(s) is/are inert filler(s), the volumizing agent(s) is/are present the compositions of the present invention in amounts of active material generally ranging from about 0.5% to about 20%, preferably from about 1% to about 15%, and preferably from about 2% to about 10%, by weight, based on the total weight of the composition, including all ranges and subranges in between.

Preferably, when the volumizing agent(s) is/are glyceryl esters of fatty acid(s), the volumizing agent(s) is/are present the compositions of the present invention in amounts of active material generally ranging from about 0.5% to about 20%, preferably from about 1% to about 15%, and preferably from about 2% to about 10%, by weight, based on the total weight of the composition, including all ranges and subranges in between.

Preferably, film-forming polymer(s) (active material) and volumizing agent(s) (inert fillers, glyceryl esters of fatty acids, or mixtures thereof) are present in the compositions of the present invention in a combined amount of 10 to 30%, preferably from 12 to 25%, and preferably from 13 to 24%, including all ranges and subranges therebetween.

Emulsification System

According to the present invention, compositions comprising an emulsification system comprising about 2% to about 6% of low HLB emulsifier(s) (HLB value less than 8), about 2% to about 8% of intermediate HLB emulsifier(s) (HLB value of 8 to 16), and about 1% to about 8% of high HLB emulsifier(s) (HLB value greater than 16), are provided.

"HLB" refers to the "hydrophilic-lipophilic balance" associated with emulsifiers. In particular, "HLB" value relates to the ratio of hydrophilic groups and lipophilic groups in emulsifiers, and also relates to solubility of the emulsifiers. Lower HLB emulsifiers are more soluble in oils (lipophilic material) and are more appropriate for use in water-in-oil (W/O) emulsions. Higher HLB emulsifiers are more soluble in water (hydrophilic material) and are more appropriate for oil-in-water (O/W) emulsions.

By way of example, the following emulsifiers have been reported to have the following HLB values:

Propylene Glycol Isostearate HLB=2.5;
Glyceryl Stearate HLB=3.8;
Sorbitan Isostearate HLB=4.7;
Oleth-2 HLB=4.9;
Glyceryl Laurate HLB=5.2;
Ceteth-2 HLB=5.3;
Methyl Glucose Sesquistearate HLB=6.6;
Laureth-4 HLB=9.7;
Cetearyl Glucoside HLB=11;
Polysorbate 85 HLB=11;
Oleth-10 HLB=12.4;
Ceteth-10 HLB=12.9;
Cocamide MEA HLB=13.5;
C12-14 pareth-12 HLB=14.5;
Polysorbate 60 HLB=14.9;
Isosteareth-20 HLB=15;
PEG-20 Methyl Glucose Sesquistearate HLB=15;
Polysorbate 80 HLB=15;
Stearic Acid HLB=15;
Ceteareth-20 HLB=15 2;
Oleth-20 HLB=15.3;
Cetyl alcohol HLB=15.5;
Behenyl alcohol HLB=15.5;
Cetearyl alcohol HLB=15.5;
Ceteth-20 HLB=15.7;
C12-13 pareth-23 HLB=16.7;
Polysorbate 20 HLB=16.7;
Laureth-23 HLB=16.9;
PEG-100 Stearate HLB=18.8; and
Sodium lauryl sulfate HLB=40.

According to preferred embodiments, one or more of the emulsifiers is a fatty alcohol, a fatty acid, or ester thereof, optionally alkoxylated (ethoxylated, propoxylated, etc.) and/or pegylated. Fatty acids correspond the formula R—COOH and fatty alcohols correspond to the formula R—OH, in which R denotes a saturated or unsaturated hydrocarbon radical preferably having from 7 to 45 carbon atoms, preferably from 9 to 35 carbon atoms, preferably from 15 to 35 carbon atoms, preferably from 15 to 21 carbon atoms, and preferably from 16 to 18 carbon atoms. Mention may be made of, for example, lauric acid/alcohol, stearic acid/alcohol, oleic acid/alcohol, behenyl acid/alcohol, and mixtures thereof.

Suitable emulsifiers include ethoxylated fatty alcohols, ethoxylated fatty acids, partial glycerides of ethoxylated fatty acids, polyglycerolated fatty acid triglycerides and ethoxylated derivatives thereof, and mixtures thereof.

Suitable alkoxylated fatty alcohols include, for example, the addition products of ethylene oxide with lauryl alcohol, in particular those containing from 9 to 250 oxyethylenated groups (e.g., having CTFA names Laureth-9 to Laureth-50); the addition products of ethylene oxide with behenyl alcohol, in particular those containing from 9 to 250 oxyethylenated groups (e.g., having CTFA names Beheneth-9 to Beheneth-50); the addition products of ethylene oxide with cetearyl alcohol (mixture of cetyl alcohol and of stearyl alcohol) in particular those containing from 9 to 250 oxyethylenated groups (e.g., having CTFA names Ceteareth-9 to Ceteareth-30); the addition products of ethylene oxide with cetyl alcohol, in particular those containing from 9 to 250 oxyethylenated groups (e.g., having CTFA names Ceteth-9 to Ceteth-30); the addition products of ethylene oxide with stearyl alcohol, in particular those containing from 9 to 30 oxyethylenated groups (e.g., having CTFA names Steareth-9 to Steareth-30; the addition products of ethylene oxide with isostearyl alcohol, in particular those containing from 9 to 250 oxyethylenated groups (e.g., having CTFA names Isosteareth-9 to Isosteareth-50); and mixtures thereof, wherein the amount of alkoxylation preferably ranges from 9 to 250, and preferably from 50 to 200, including all ranges and subranges therebetween including, for example, 100 to 200, 50 to 100, etc.

Suitable alkoxylated fatty acid include, for example, the addition products of ethylene oxide with lauric acid, palmitic acid, stearic acid or behenic acid, and mixtures thereof, in particular those containing from 9 to 250 oxyethylenated groups, such as laurates of PEG-9 to PEG-50 (e.g., having CTFA names: PEG-9 laurate to PEG-50 laurate); palmitates of PEG-9 to PEG-50 (e.g., having CTFA names: PEG-9 palmitate to PEG-50 palmitate); stearates of PEG-9 to PEG-250 (e.g., having CTFA names: PEG-9 stearate to PEG-250 stearate such as PEG-100 stearate to PEG-200 stearate); palmitostearates of PEG-9 to PEG-50; behenates of PEG-9 to PEG-50 (e.g., having CTFA names: PEG-9 behenate to PEG-50 behenate); and mixtures thereof, wherein the amount of alkoxylation preferably ranges from 9 to 250, and preferably from 50 to 200, including all ranges and subranges therebetween including, for example, 100 to 200, 50 to 100, etc.

Preferably, about 2% to about 6% of low HLB emulsifier(s) (HLB value less than 8), about 2% to about 8% of intermediate HLB emulsifier(s) (HLB value of 8 to 16), and about 1% to about 8% of high HLB emulsifier(s) (HLB value greater than 16) by weight are present in the compositions of the present invention, based on the total weight of the composition, including all ranges and subranges in between.

Preferably, about 2% to about 5% of low HLB emulsifier(s) (HLB value less than 8), about 2% to about 8% of intermediate HLB emulsifier(s) (HLB value of 8 to 16), and about 1% to about 2% of high HLB emulsifier(s) (HLB value greater than 16) by weight are present in the compositions of the present invention, based on the total weight of the composition, including all ranges and subranges in between.

Preferably, low HLB emulsifier(s) and intermediate HLB emulsifier(s) are present in the compositions of the present invention in a weight ratio of from 6:1 to 1:6, preferably from 4:1 to 1:4, and preferably from 3:1 to 1:4, including all ranges and subranges therebetween.

Preferably, low HLB emulsifier(s) and high HLB emulsifier(s) are present in the compositions of the present invention in a weight ratio of from 6:1 to 1:6, preferably from 5:1 to 1:5, and preferably from 3:1 to 1:3, including all ranges and subranges therebetween.

Preferably, intermediate HLB emulsifier(s) and high HLB emulsifier(s) are present in the compositions of the present invention in a weight ratio of from 10:1 to 1:5, preferably from 6:1 to 1:4.52, and preferably from 5:1 to 1:4, including all ranges and subranges therebetween.

Oil Phase

According to embodiments of the present invention, the compositions of the present invention may optionally further comprise at least one oil. "Oil" means any non-aqueous medium which is liquid at ambient temperature (25° C.) and atmospheric pressure (760 mm Hg).

Suitable oils include volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms. Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Suitable oils include non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_5$ to $C_{16}$ alkanes such as $C_5$ to $C_{16}$ isoalkanes (also known as isoparaffins), isododecane, isodecane, and for example, the oils sold under the trade names of Isopar or Permethyl. Preferably, the volatile non-silicone oils have a flash point of at least 40° C.

Suitable oils include synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; pentaerythritol esters; and synthetic ethers containing from 10 to 40 carbon atoms.

If present, the oil(s) is/are present in the compositions of the present invention in an amount ranging from about 0.1% to about 30% by weight, more preferably from about 1% to about 25% by weight, and preferably from about 3% to about 20% by weight, based on the total weight of the composition, including all ranges and subranges within these ranges.

According to embodiments of the present invention, the compositions of the present invention may further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C., silicone waxes, such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, or else di(1,1,1-trimethylolpropane) tetrastearate, which is sold or manufactured by Heterene under the name HEST 2T-4S, and mixtures thereof.

If present, the wax or waxes are preferably present in an amount ranging from about 0.1% to about 5% by weight, preferably from about 0.1% to about 3% by weight, and preferably from about 0.1% to about 1% by weight, based on the total weight of the composition, including all ranges and subranges within these ranges. However, according to particularly preferred embodiments of the present invention, the compositions of the present invention are wax-free.

Coloring Agents

According to preferred embodiments of the present invention, compositions optionally further comprising at least one coloring agent are provided. Preferably, such colored compositions can be cosmetic compositions such as mascaras.

According to this embodiment, the at least one coloring agent is preferably chosen from pigments, dyes, such as liposoluble dyes, nacreous pigments, and pearling agents.

Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow. The liposoluble dyes, when present, generally have a concentration ranging up to 20% by weight of the total weight of the composition, such as from 0.0001% to 6%, including all ranges and subranges therebetween.

The nacreous pigments which may be used according to the present invention may be chosen from white nacreous pigments such as mica coated with titanium or with bismuth oxychloride, colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, may be present in the composition in a concentration ranging up to 50% by weight of the total weight of the composition, such as from 0.1% to 20%, preferably from 0.1% to 15%, including all ranges and subranges therebetween.

The pigments, which may be used according to the present invention, may be chosen from white, colored, inorganic, organic, polymeric, nonpolymeric, coated and uncoated pigments. Representative examples of mineral pigments include titanium dioxide, optionally surface-treated, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the pigments may be present in the composition in a concentration ranging up to 50% by weight of the total weight of the composition, such as from 0.5% to 40%, and further such as from 2% to 30%, including all ranges and subranges therebetween. In the case of certain products, the pigments, including nacreous pigments, may, for example, represent up to 50% by weight of the composition.

Additional Additives

The composition of the invention can also comprise any additive usually used in the field under consideration. For example, dispersants such as poly(12-hydroxystearic acid), antioxidants, film forming agents, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, pasty compounds, viscosity increasing agents such as waxes or liposoluble/lipodispersible polymers, and mixtures thereof can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* (9th ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the eyelashes of human beings.

According to preferred embodiments of the present invention, methods of treating, caring for and/or making up keratinous material such as skin, lips, eyes and eyelashes by applying compositions of the present invention to the keratinous material in an amount sufficient to treat, care for and/or make up the keratinous material are provided. Preferably, "making up" the keratin material includes applying at least one coloring agent to the keratin material in an amount sufficient to provide color to the keratin material.

According to yet other preferred embodiments, methods of enhancing the appearance of keratinous material by applying compositions of the present invention to the keratinous material in an amount sufficient to enhance the appearance of the keratinous material are provided.

According to yet other preferred embodiments, methods of volumizing eyelashes and/or eyebrows by applying compositions of the present invention to the eyelashes and/or eyebrows in an amount sufficient to enhance the appearance of the eyelashes and/or eyebrows are provided.

In accordance with the preceding preferred embodiments, the compositions of the present invention are applied topically to the desired area of the keratin material in an amount sufficient to treat, care for and/or make up the keratinous material, or to enhance the appearance of keratinous material or to volumize eyelashes and/or eyebrows. The compositions may be applied to the desired area as needed, preferably once or twice daily, more preferably once daily and then preferably allowed to dry before subjecting to contact such as with clothing or other objects (for example, a topcoat). Preferably, the composition is allowed to dry for about 1 minute or less, more preferably for about 45 seconds or less. The composition is preferably applied to the desired area that is dry or has been dried prior to application, or to which a basecoat has been previously applied.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example I—Sample Formulation

| Ingredient | Weight % |
|---|---|
| Film Formers | 7%-20% (active material) |
| Low - HLB emulsifier | 2-6% |
| Intermediate HLB emulsifier | 2-8% |
| High HLB Emulisifer | 1-8% |
| Volumizing Agent | 2-10% |
| Pigments | 3-20% |
| water | 40-90% |

Example II—Formulations Preparation

[The compositions in Example III were prepared in the following manner:

Water was heated to 60-70° C. with agitation using a large chopping blade (100 rpm).

Water was charged with pigments, preservatives, water-soluble thickeners, water-soluble emulsifiers, and plasticizers, and mixed with a large rotor-stator homogenizer at 500-900 rpm until pigments dispersed (approx. 1 hr).

Oils, oil-soluble emulsifiers and oil-soluble film-formers were melted at 70-90° C. and added to water phase using large rotor-stator homogenizer at 900-1200 rpm and emulsified for 30 minutes at 70-80° C. Shea butter, if added, can be added at this time or added alone prior to emulsification without melting.

Once emulsified, the composition was cooled to 50-60° C.

Temperature film-former dispersions were then added and mixed for 20 minutes (1200 rpm).

The homogenizer can be left on or stopped at this time.

Once internal temperature reached 30-40° C., the bulk was poured.

Example III—Actual Formulations

Reference Example 1 and Invention Examples 2 through 12 were prepared:

| Ingredient | Ex. 2 | Ex. 3 | Ex. 4 | Ex. 5 | Ex. 6 | Ex. 7 | Ex. 8 | Ref 1 |
|---|---|---|---|---|---|---|---|---|
| Film Formers | 12.06 | 12.06 | 16.08 | 12.06 | 12.06 | 12.06 | 12.06 | 12.06 |
| Volumizer (Shea Butter) | 4.99 | 4.99 | 4.99 | 4.99 | 4.99 | 4.99 | 4.99 | |
| Oil/Liquid Fatty Substance | 4 | 4 | 4 | 4 | 4 | 4 | 4 | 8.99 |

|  | Ingredient | | | | | | | | |
|---|---|---|---|---|---|---|---|---|---|
|  | Oil Phase Gellant | 2.5 | 2.5 | 2.5 | 2.5 | 2.5 | 2.5 | 2.5 | 2.5 |
| Intermediate HLB emulsifier (8-16) | BEHENYL ALCOHOL | 1.75 | 1.75 | 1.75 | 1.75 | 1.75 | 1.75 | 1.75 | 1.75 |
|  | GLYCERYL STEARATE CITRATE | 0.75 | 0.75 | 0.75 | 0.75 | 0.75 | 0.75 | 0.75 | 0.75 |
| Low HLB emulsifier (1-8) | GLYCERYL STEARATE GLYCERYL STEARATE | 2.25 | 2.25 | 4.25 | 4.25 | 4.25 | 4.25 | 3.25 | 2.25 |
|  | Preservative or Antioxidant or Plasticizer, pH Adjuster | 17.01 | 17.01 | 17.01 | 17.0 | 17.01 | 17.01 | 17.01 | 17.01 |
|  | Water | 46.069 | 52.269 | 43.9 | 48.26 | 45.169 | 42.069 | 44.069 | 45.96 |
| High HLB Emulsifiers (>16) | SODIUM LAURETH SULFATE C12-13 PARETH-3 C12-13 PARETH-23 DISODIUM ETHYLENE DICOCAMIDE PEG-15 DISULFATE PEG-200 GLYCERYL STEARATE PEG-100 STEARATE | 7.21 | 1.01 | 1.01 | 1.01 | 4.11 | 7.21 | 7.21 | 7.21 |
|  | Water phase gellant | 0.787 | 0.787 | 0.787 | 0.787 | 0.787 | 0.787 | 0.787 | 0.787 |

|  | Ingredient | Ex. 9 | Ex. 10 | Ex. 11 | Ex. 12 |
|---|---|---|---|---|---|
|  | Film formers | 16.25 | 16.25 | 16.25 | 12.06 |
|  | Pigment, Preservative plasticizers | 16.84 | 16.84 | 16.84 | 16.84 |
|  | Oil Phase Gellant | 2.5 | 2.5 | 2.5 | 2.5 |
| Low HLB Emulsifier | GLYCERYL STEARATE GLYCERYL STEARATE | 2.25 | 2.25 | 4.25 | 2.25 |
| Intermediate HLB Emulsifier | GLYCERYL STEARATE CITRATE | 0.75 | 0.75 | 0.75 | 0.75 |
|  | BEHENYL ALCOHOL | 1.75 | 1.75 | 1.75 | 1.75 |
|  | CETYL ALCOHOL | 5 |  |  | 5 |
|  | WATER | 42.402 | 47.402 | 43.402 | 47.369 |
| Volumizing Agent | PTFE | 6 | 6 | 6 |  |
|  | BUTYROSPERMUM PARKII (SHEA) BUTTER |  |  |  | 5 |
| High HLB Emulsifier | PEG-100 STEARATE | 0.5 | 0.5 | 2.5 | 0.5 |
|  | C12-13 PARETH-3 | 0.042 | 0.042 | 0.042 | 0.042 |
|  | C12-13 PARETH-23 | 0.042 | 0.042 | 0.042 | 0.042 |
|  | SODIUM LAURETH SULFATE | 0.135 | 0.135 | 0.135 | 0.18 |
|  | DISODIUM ETHYLENE DICOCAMIDE PEG-15 DISULFATE | 0.75 | 0.75 | 0.75 | 0.75 |
|  | Liquid Fatty Substance | 0.48 | 0.48 | 0.48 | 0.48 |
|  |  | 3.28 | 3.28 | 3.28 | 3.28 |
|  |  | 0.24 | 0.24 | 0.24 | 0.24 |
|  | Water Phase gellant | 0.787 | 0.787 | 0.787 | 0.787 |

Example IV—Commercial Product

Commercial Product A: Water, Propylene Glycol, Styrene/Acrylates/Ammonium Methacrylate Copolymer, Polyurethane-35, Cera Alba/Beeswax/Cire Dabeille, Synthetic Fluorphlogopite, Glyceryl Stearate, Cetyl Alcohol, PEG-200 Glyceryl Stearate, Ethylenediamine/Stearyl Dimer Dilinoleate Copolymer, Copernicia Cerifera Cera/Carnauba Wax/Cire de Carnauba, Stearic Acid, Palmitic Acid, Ethylene/Va Copolymer, Alcohol Denat., Paraffin, Aminomethyl Propanediol, Glycerin, Hydroxyethylcellulose, Phenoxyethanol, Caprylyl Glycol, Butylene Glycol, Xanthan Gum, Sodium Laureth Sulfate, Disodium EDTA, Tetrasodium EDTA, Pentaerythrityl Tetra-Di-T-Butyl Hydroxyhydrocinnamate, Silica. May Contain: CI 77491, CI 77492, CI 77499/Iron Oxides, CI 77007/Ultramarines, CI 77891/Titanium Dioxide, MICA, CI 75470/Carmine, CI 77288/Chroinium Oxide Greens, CI 77747/Manganese Violet, CI 77510/Ferric Ferrocyanide].

Example V—Testing Protocols

Formulas were prepared and analyzed in vitro in an extreme flake test on fake eyelashes after a 1 hour dry time. Further formula characterization was done by rheology, texture analysis to determine the impact of the modification on the texture, and consistency. The results were then compared to Reference 1 formula, without shea butter, and to Commercial Product A. The following testing methods were used.

Strain Sweep Determination:

Strain Sweep was determined on a DHR-2 Rheometer from TA Instruments with a 40 mm 2° cone at 20° C. from 0.01-1000% strain at 1 rad/s.

Texture Analysis:

Experiments were performed on a TA.XT Plus Texture Analyzer with a cylindrical TA-Delrin probe (10 mm diameter) in 6×2 cm stainless steel cups, filled with bulk at 25° C. Surface cut with stainless steel blade to ensure flat top surface. Settings: Test Mode: compression, Pre-test speed: 2 mm/sec, post-test speed: 2 mm/sec, test speed: 0.5 mm/sec, target mode: distance, distance: 5 mm, trigger force: auto, trigger force: 2 grams. After penetrating the sample the probe returned to its initial position. The curve generated is a plot of force (grams) as a function of time (seconds). When a 2 g surface trigger was attained, the probe proceeds to penetrate to a depth of 5 mm. At this point (maximum +ve force), the probe returns to its original position at constant speed (e.g. 2.0 mm/s). The maximum+ve force (hardness, grams) gave an indication of the softness of the sample. The smaller the peak force value, the softer sample. Data repeated in triplicate.

Extreme Removal:

Experiments were run in triplicate. 30 strokes of product were applied to fake eyelashes in 15 stroke sets, 30 second 16-24 hours. Samples allowed to dry for 1 hour. Cotton pads were soaked with 1.5 mL of water. Fake lash was held between the cotton pad for 10 seconds then withdrawn gently. Process repeated until no additional product removed. The number of pads to remove the mascara completely were counted. The less the number of pads, the easier the mascara was to remove with water.

Extreme Flake:

Experiments were run in triplicate. 30 strokes of product were applied to fake eyelashes in 15 stroke sets with a 30 second pause between second application. Samples allowed to dry 1 hour. Sample was held in place in a polystyrene weigh boat and brushed 10 times with a dry bristle mascara brush. Flakes were collected with tape and rated comparatively.

Example VI—Testing Results

Critical Strain:

Critical Strain was determined in a strain sweep. Data compiled below demonstrated a trend with regard to the respective examples versus the Reference formula containing oils and a non-optimal emulsification system.

| Ex. | Ratio B** | Ratio A* | % Total Film Former | % Fat (Butter or Oil) | % Filler | Critical Strain (Method A, %) |
|---|---|---|---|---|---|---|
| Ref 1 | 1:3.92 | 1:3 | 12.06 | 5 | | 11.5 |
| Ex. 5 | 1.2:1 | 1:1.4 | 12.06 | 4.99 | | 2.75 |
| Ex. 6 | 1:1.5 | 1:2.6 | 12.06 | 4.99 | | 4.40 |
| Ex. 7 | 1:2.3 | 1:3.8 | 12.06 | 4.99 | | 7.24 |
| Ex. 10 | 1.6:1 | 15:1 | 16.25 | | 6 | 2.75 |
| Ex. 11 | 1:2 | 1:1.2 | 16.25 | | 6 | 4.35 |

*Ratio A = ratio (sum of low HLB emulsifiers):(sum of high HLB emulsifiers)
**Ratio B = ratio (sum of intermediate HLB emulsifiers):(sum of high HLB emulsifiers).

The data from the above table is repeated below in the context of key pegylated emulsifiers present:

| Ex. | PEG-200 GS | PEG-100 GS | GS | Int. HLB | % Fat (Butter or Oil) | % Filler | Critical Strain (%) |
|---|---|---|---|---|---|---|---|
| Ref. 1 | 6.2 | 0.5 | 2.25 | 2.5 | 4.99 | 0 | 11.5 |
| Ex. 5 | 0 | 2.5 | 4.25 | 2.5 | 4.99 | 0 | 2.75 |
| Ex. 6 | 3.1 | 2.5 | 4.25 | 2.5 | 4.99 | 0 | 4.40 |
| Ex. 7 | 6.2 | 2.5 | 4.25 | 2.5 | 4.99 | 0 | 7.24 |
| Ex. 9 | 0 | 0.5 | 2.25 | 7.5 | 0 | 6 | 2.88 |
| Ex. 10 | 0 | 0.5 | 2.25 | 2.5 | 0 | 6 | 2.75 |
| Ex. 11 | 0 | 2.5 | 4.25 | 2.5 | 0 | 6 | 4.35 |

Invention compositions showed the critical strain (>4%) increased with higher levels (>3%) of PEG-200 stearate (Ex. 6 and 7 and Ref. 1). The volumizer is the raw material in the formula that causes more mascara to be left on the keratinous fibers creating darker, more volumized lashes. Alternatively, critical strains of less than 4% could be achieved with PEG-100 stearate at a maximum use level of 2.5% (Ex. 5). Further increasing the level of low HLB emulsifier (glyceryl stearate) or intermediate HLB emulsifier (cetyl alcohol) did not detrimentally increase the critical strain in formulas with PEG-100 stearate (Ex. 9-11).

Unexpectedly lower critical strains were observed with glyceryl stearate to PEG-100 stearate weight ratios from 1.5:1 to 5:1, as well as with intermediate HLB emulsifier to PEG-100 stearate weight ratios from 1:1 to 15:1 in the absence of PEG-200 stearate.

Texture:

The impact of emulsifier levels on texture as determined by penetration experiment described above was tested. The data below demonstrated a trend with regard to the respective examples versus the Reference formula with oils and a non-optimal emulsification system.

| Ex. | PEG-200 GS | PEG-100 GS | GS | Int. HLB | % Fat (Butter or Oil) | % Filler | Hardness (g) |
|---|---|---|---|---|---|---|---|
| Ref 1 | 6.2 | 0.5 | 2.25 | 2.5 | 4.99 | 0 | 21.3 |
| Ex. 2 | 6.2 | 0.5 | 2.25 | 2.5 | 4.99 | 0 | 12.4 |
| Ex. 3 | 0 | 0.5 | 2.25 | 2.5 | 4.99 | 0 | 11.3 |
| E. 4 | 0 | 2.5 | 4.25 | 2.5 | 4.99 | 0 | 45.3 |
| Ex. 5 | 0 | 2.5 | 4.25 | 2.5 | 4.99 | 0 | 34.4 |
| Ex. 6 | 3.1 | 7.5 | 4.25 | 2.5 | 4.99 | 0 | 31.8 |
| Ex. 7 | 6.2 | 2.5 | 4.25 | 2.5 | 4.99 | 0 | 58.7 |
| Ex. 8 | 6.2 | 1.5 | 3.25 | 2.5 | 4.99 | 0 | 23.0 |
| Ex. 9 | 0 | 0.5 | 2.25 | 7.5 | 0 | 6 | 65.22 |
| Ex. 10 | 0 | 0.5 | 2.75 | 2.5 | 0 | 6 | 26.17 |
| Ex. 11 | 0 | 2.5 | 4.25 | 2.5 | 0 | 6 | 80.08 |

As reflected above, the hardness of the invention compositions could be increased by increasing the level of the low HLB emulsifier (GS=glyceryl stearate) and intermediate HLB emulsifiers as compared to pegylated glyceryl stearate (PEG-100 stearate and PEG-200 stearate). For example, hardness could be increased about two-fold by increasing low HLB emulsifier content by about 1.7-fold and intermediate HLB emulsifier content by about 3-fold in the presence of 2.5% PEG-100 stearate (see, Examples 2-5 and 9). Increasing the hardness of the cosmetic compositions effectively reduces the feeling of wetness during application to the lashes and allows the formula to behave more like a traditional mascara with waxes despite the fact that these formulae do not contain waxes. Adding PEG-200 stearate to compositions containing a high level of low HLB emulsifiers further increased hardness (see, Examples 6-8).

Extreme removal and Extreme Flake:

Extreme flake and removal tests were performed. Flaking was visually rated on a scale from 1-5 (low flake to high flake). A rating of 1 was given for mascaras that did not flake a lot. Both tests were performed as described above.

| Ex. | PEG-200 GS | PEG-100 GS | GS | % Total Film Former | % Fat (Butter or Oil) | % Filler | Removal (# pads) | Flake Rating |
|---|---|---|---|---|---|---|---|---|
| Ex. 2 | 6.2 | 0.5 | 2.25 | 12.06 | 4.99 | 0 | 2.35 | 4 |
| Ex. 3 | 0 | 0.5 | 2.25 | 12.06 | 4.99 | 0 | 2.1 | 3.5 |
| Ex. 4 | 0 | 2.5 | 4.25 | 16.08 | 4.99 | 0 | 2.2 | 3 |
| Ex. 5 | 0 | 9.5 | 4.25 | 12.06 | 4.99 | 0 | 2.25 | 3 |
| Ex. 6 | 3.1 | 9.5 | 4.25 | 12.06 | 4.99 | 0 | 1.7 | 4 |
| Ex. 7 | 6.2 | 2.5 | 4.25 | 12.06 | 4.99 | 0 | 2.2 | 3 |
| Ex. 8 | 6.2 | 1.5 | 3.25 | 12.06 | 4.99 | 0 | 2.15 | 5 |

Attenuation of the ratios of the emulsifiers did not significantly impact the number of pads to remove the product from fake lashes. This was surprising given that increasing low HLB emulsifiers typically increases smudging upon removal. In terms of flaking, increasing the levels of latex film-forming agent reduced flaking. (Ex.4). It was unexpected that there was a trend of increase in flaking in the presence of high levels of PEG-200 stearate (Exs. 2 and 8) and a trend of decrease in flaking with PEG-100 stearate. The optimal level appeared to be at a ratio of from 4.5:1 to 1.7:1 of Glyceryl Stearate to PEG-100 stearate (Ex. 5). This result was not impacted by the addition of the PEG-200 stearate (Ex. 7).

Example VII—Preferred Processing Conditions

Invention composition Ex. 5 was prepared at various processing conditions, particularly different drop temperatures, and the effect on the resulting hardness of the compositions. Results are set forth below:

| DoE Ref 1 | Cooling rate ° C. at a time | Emulsification time (2000 RPM) | Drop T | Hardness (g) |
|---|---|---|---|---|
| 1 | 5 | 30 | 30 | 35.1 |
| 11 | 12 | 30 | 35 | 23.6 |
| 7 | 2.5 | 30 | 40 | 55.6 |

An optimal emulsification time of 30 min with slow cooling and a drop temperature of 40° C. resulted in a preferred formulation having a hardness of greater than 40 g.

What is claimed is:

1. A composition comprising water, at least one dispersion of film forming particles in aqueous phase, at least one volumizing agent which is shea butter, and an emulsification system comprising about 2% to about 6% of low HLB emulsifier(s), about 2% to about 8% of intermediate HLB emulsifier(s), and about 1% to about 8% of high HLB emulsifier(s) by weight with respect to the total weight of the composition.

2. The composition of claim 1, wherein the composition is a mascara.

3. The composition of claim 1, wherein the composition is wax-free.

4. The composition of claim 1, further comprising at least one colorant.

5. The composition of claim 1, further comprising at least one volumizing agent which is a filler.

6. The composition of claim 5, wherein the at least one volumizing agent is polytetrafluoroethylene.

7. The composition of claim 1, wherein the shea butter is present in the composition in an amount of about 2% to about 10% by weight with respect to the total weight of the composition.

8. The composition of claim 1, wherein water is present in the composition in an amount of about 30% to about 60% by weight with respect to the total weight of the composition.

9. The composition of claim 1, in the form of an oil-in-water emulsion.

10. The composition of claim 8, in the form of an oil-in-water emulsion.

11. The composition of claim 1, wherein the low HLB emulsifier(s) and the intermediate HLB emulsifier(s) are present in a weight ratio of from 3:1 to 1:4.

12. The composition of claim 1, wherein the low HLB emulsifier(s) and the high HLB emulsifier(s) are present in a weight ratio of from 3:1 to 1:3.

13. The composition of claim 1, wherein the intermediate HLB emulsifier(s) and the high HLB emulsifier(s) are present in a weight ratio of from 20:1 to 1:3.

14. The composition of claim 1, wherein: the low HLB emulsifier(s) and the intermediate HLB emulsifier(s) are present in a weight ratio of from 3:1 to 1:4; the low HLB emulsifier(s) and the high HLB emulsifier(s) are present in a weight ratio of from 3:1 to 1:3; and the intermediate HLB emulsifier(s) and the high HLB emulsifier(s) are present in a weight ratio of from 5:1 to 1:4.

15. The composition of claim 14, wherein the composition is wax-free.

16. The composition of claim 14, wherein the composition is a mascara.

17. The composition of claim 1, further comprising at least one wax in an amount ranging from about 0.1% to about 5% by weight based on the total weight of the composition.

18. The composition of claim 14, further comprising at least one wax in an amount ranging from about 0.1% to about 5% by weight based on the total weight of the composition.

19. A method of making up eyelashes comprising applying the composition of claim 1 to the eyelashes.

20. A method of making up eyelashes comprising applying the composition of claim 16 to the eyelashes.

* * * * *